United States Patent
Micheau-Cunningham et al.

(10) Patent No.: US 9,784,715 B2
(45) Date of Patent: Oct. 10, 2017

(54) EDDY CURRENT INSPECTION PROBE BASED ON MAGNETORESISTIVE SENSORS

(71) Applicant: Zetec, Inc., Snoqualmie, WA (US)

(72) Inventors: Jevne Branden Micheau-Cunningham, Seattle, WA (US); Jeffrey Raymond Gueble, Bainbridge Island, WA (US); William Frederick Ziegenhagen, Kent, WA (US); Stephen Timm, Bellevue, WA (US); Paubla Mejia Tarango, Renton, WA (US)

(73) Assignee: ZETEC, INC., Snoqualmie, WA (US)

( * ) Notice: Subject to any disclaimer, the term of this patent is extended or adjusted under 35 U.S.C. 154(b) by 211 days.

(21) Appl. No.: 14/255,272

(22) Filed: Apr. 17, 2014

(65) Prior Publication Data

US 2014/0312891 A1    Oct. 23, 2014

Related U.S. Application Data (60) Provisional application No. 61/813,899, filed on Apr. 19, 2013.

(51) Int. Cl.
  *G01N 27/82* (2006.01)
  *G01N 27/90* (2006.01)
  *G01R 33/09* (2006.01)

(52) U.S. Cl.
  CPC ....... *G01N 27/904* (2013.01); *G01N 27/9033* (2013.01); *G01R 33/09* (2013.01)

(58) Field of Classification Search
  CPC .... G01N 27/904; G01N 27/82; G01N 27/902; G01R 33/09

(Continued)

(56) References Cited

U.S. PATENT DOCUMENTS 3,694,740 A * 9/1972 Bergstrand .......... G01N 27/902
                                                              324/227
3,875,502 A    4/1975 Neumaier
(Continued)

FOREIGN PATENT DOCUMENTS

JP    2006322860    11/2006
WO    2008/054056 A1    5/2008

OTHER PUBLICATIONS

"Single-Axis Magnetic Sensor HMC1021D", datasheet, Oct. 1, 2005, pp. 1-4, XP055126282, Retrieved from the Internet: URL:http://www.sssj.co.jp/products/magnetic/pdf/hmc1021d.pdf.

(Continued)

*Primary Examiner* — Tung X Nguyen
*Assistant Examiner* — Dominic Hawkins
(74) *Attorney, Agent, or Firm* — Snyder, Clark, Lesch & Chung, LLP (57) ABSTRACT

A device and method of eddy current based nondestructive testing of tubular structures made of electrically conductive materials is disclosed. The device includes a plurality of excitation electromagnets having an axis of symmetry and magnetoresistive sensors having an easy axis for magnetic field sensing; wherein the magnetoresistive sensors are arranged in a circular array on a single plane with the easy axis aligned radially with respect to the circular pattern and wherein the electromagnets are arranged in a circular pattern on both sides of the plane with their axes of symmetry being arranged parallel to the plane and orthogonal to radii of the circular pattern on which the electromagnets are placed.

15 Claims, 11 Drawing Sheets

(58) Field of Classification Search
USPC .......................................... 324/242, 240, 244
See application file for complete search history.

(56) References Cited

U.S. PATENT DOCUMENTS

| | | | | |
|---|---|---|---|---|
| 5,696,449 | A * | 12/1997 | Boskamp | G01R 33/34061 324/318 |
| 5,929,636 | A | 7/1999 | Torok et al. | |
| 6,150,809 | A | 11/2000 | Tiernan et al. | |
| 6,356,074 | B1 * | 3/2002 | Ohkawa | G01B 7/30 324/174 |
| 6,448,773 | B1 * | 9/2002 | Zhang | G01R 33/56518 324/307 |
| 6,504,363 | B1 * | 1/2003 | Dogaru | G01N 27/9006 324/235 |
| 6,577,121 | B1 * | 6/2003 | Adelerhof | G01D 5/145 324/207.21 |
| 6,693,425 | B2 | 2/2004 | Wache | |
| 6,888,346 | B2 | 5/2005 | Wincheski et al. | |
| 6,933,717 | B1 | 8/2005 | Dogaru et al. | |
| 7,235,967 | B2 | 6/2007 | Nishimizu et al. | |
| 7,250,757 | B1 | 7/2007 | Tiernan et al. | |
| 7,304,474 | B2 | 12/2007 | Rempt | |
| 7,355,822 | B2 | 4/2008 | Daughton et al. | |
| 7,542,871 | B2 | 6/2009 | Rempt et al. | |
| 7,952,348 | B2 | 5/2011 | Sun et al. | |
| 8,049,495 | B2 | 11/2011 | Beller et al. | |
| 8,063,631 | B2 | 11/2011 | Fermon et al. | |
| 8,274,276 | B2 | 9/2012 | Kreutzbruck et al. | |
| 8,344,725 | B2 | 1/2013 | Fischer et al. | |
| 8,368,395 | B2 | 2/2013 | Weischedel | |
| 8,432,158 | B2 * | 4/2013 | Bussan | G01P 3/488 324/173 |
| 2002/0130659 | A1 * | 9/2002 | Wincheski | G01N 27/9033 324/235 |
| 2002/0158626 | A1 * | 10/2002 | Shay | G01N 27/902 324/207.16 |
| 2004/0021461 | A1 * | 2/2004 | Goldfine | G01V 3/15 324/243 |
| 2005/0007108 | A1 | 1/2005 | Dogaru | |
| 2005/0205251 | A1 * | 9/2005 | Tulloch | E21B 37/02 166/173 |
| 2006/0290349 | A1 * | 12/2006 | Na | G01N 27/9033 324/228 |
| 2006/0291106 | A1 * | 12/2006 | Shoji | G01R 33/09 360/324.11 |
| 2007/0120560 | A1 * | 5/2007 | Rempt | G01N 27/82 324/238 |
| 2008/0111544 | A1 * | 5/2008 | Patland | H01F 7/20 324/232 |
| 2008/0179183 | A1 * | 7/2008 | Boitnott | H01J 37/3408 204/192.35 |
| 2010/0085040 | A1 * | 4/2010 | Bussan | G01P 3/488 324/207.21 |
| 2010/0117638 | A1 * | 5/2010 | Yamashita | G01R 33/07 324/233 |
| 2010/0148766 | A1 * | 6/2010 | Weischedel | G01N 27/9033 324/238 |
| 2011/0068784 | A1 | 3/2011 | Sun et al. | |
| 2012/0019236 | A1 | 1/2012 | Tiernan et al. | |
| 2012/0119732 | A1 * | 5/2012 | Rose | G01N 29/2412 324/240 |
| 2012/0274319 | A1 | 11/2012 | Wincheski et al. | |
| 2013/0214771 | A1 * | 8/2013 | Tiernan | G01N 33/383 324/242 |
| 2016/0025680 | A1 * | 1/2016 | Schein, Jr. | G01N 27/82 324/228 |
| 2016/0084800 | A1 * | 3/2016 | Michaeu-Cunningham | G01N 27/904 324/242 |

OTHER PUBLICATIONS

International Search Report for PCT/US2014/034479 dated Jul. 9, 2014.

* cited by examiner

EDDY CURRENT INSPECTION PROBE BASED ON MAGNETORESISTIVE SENSORS

CROSS-REFERENCE TO RELATED APPLICATIONS

This utility application claims the benefit under 35 U.S.C. §119(e) of provisional application Ser. No 61/813,899 filed on Apr. 19, 2013, and entitled Eddy Current Inspection Probe for Imaging Magnetic Flux Leakage of Flaws and Points of Interest in Tubular Structures Based on Magnetoresistive Sensors. The entire disclosure of this provisional application is included herein by reference.

FIELD OF THE INVENTION

The invention is directed to sensor probes for eddy current non-destructive testing and, in particular, to such probes employing magnetoresistive sensors.

BACKGROUND OF THE INVENTION

Nondestructive evaluation (NDE) technologies have been recently challenged to find material defects such as fatigue flaws, cracks and damage precursors such as stress or corrosion induced local conductivity variation in structures with higher probability of detection (POD) and a level of improvement is necessary as these issues are critical to operational safety. Certain inspection opportunities and their specific geometries often necessitate off-the-surface or non-contact methodologies thereby eliminating methods such as ultrasound testing where either physical contact or a transmit medium necessary for inspection. The non-destructive testing industry currently does most non-contact inspection of conductive materials via conventional wound inductive coil based eddy current inspection techniques. These inspections have limited spatial resolution due to sense coil size as well as frequency dependent sensitivity and thus have limited efficacy.

Eddy current testing (ECT) probes to locate and characterize flaws or material defects in a conductive material are known. An ECT probe does this by sensing the out-of-plane magnetic flux leakage (MFL) created by the deviation of eddy currents by the flaws or defects in the area under test (AUT).

Technological advancements in the manufacturing of these elements have led to commercially accessible sensing elements. Low cost anisotropic magnetoresistance AMR and giant magnetoresistive GMR magnetometers (referred to collectively as "XMR" sensors herein) are now available which are sensitive, have small package size, consume little power, and operate at room temperature.

ECT utilizing XMR sensing can have a higher level of utility, as these sensing elements are non-inductive and orders of magnitude smaller than traditional eddy current coils. A magnetoresistive (MR) sensor is a solid-state device that utilizes electron conduction physics to convert a magnetic field into an electrical signal. Anisotropic magnetoresistance (AMR), for example, is a solid-state sensing element that has a permalloy (Ni80—Fe20) electrodeposited line on silicon for sensing low-level magnetic fields. This occurs by an alignment of the material's magnetic domains in response to the external magnetic field of interest. This magnetic domain alignment changes the resistivity of the sensor via induced changes in the scattering matrix (spin-coupled interaction between the conduction electrons and the magnetic moments in the material)). In contrast a magnetic sensor exhibiting the giant magnetoresistive (GMR) mechanism will convert a sensed magnetic field to an electrical signal is exploiting the spin-coupled charge interaction of a multi-layer structure. This structure is a three-ply stack of a ferromagnetic material (FM), a non-magnetic conductive layer (NM) and a bottom layer of ferromagnetic material (FM) all on a silicon substrate.

Figure 1:
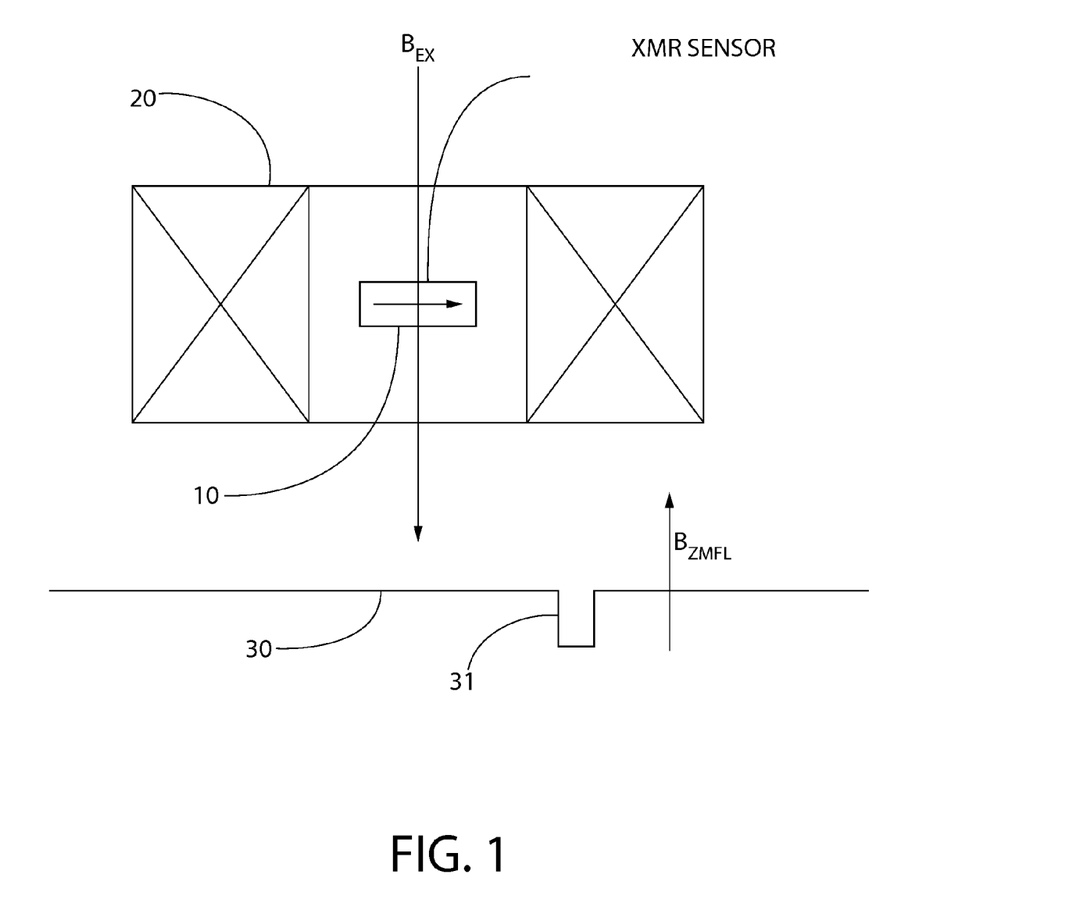
FIG. 1 is a diagram of a prior art eddy current testing probe showing an XMR sensor with easy axis parallel to $B_{EX}$.

One of the challenges with XMR sensors is that they have no means of discriminating magnetic fields sensed along the easy axis. Because the level of the field of interest will be orders of magnitude lower than the background drive magnetic field, it has been historic precedent to either: (a) shield the sensor from the drive field or (b) orient the sensor such that the sensitive axis is orthogonal to the drive field as to not saturate the sensing element. For example, one can find the use of concentric/co-located sensors and drives in U.S. patents: U.S. Pat. No. 6,888,346, 2011/0068784 A1, 2005/0007108 A1, U.S. Pat. No. 6,888,346 as well as 2005/0007108 A1. All of the documents cited herein are incorporated by reference in their entireties. This has led to the vast majority of embodied XMR based ECT probes towards using the sensor in a horizontal sensing configuration with respect to the AUT while positioned in the center of an excitation coil. As illustrated in FIG. 1, this allows the sensor 10 to be co-located with the drive coil 20 and positioned in the bore of the coil orienting the excitation field $B_{EX}$ orthogonally to the sensor easy axis. Therefore the sensor would be immune to the excitation field.

Figure 2:
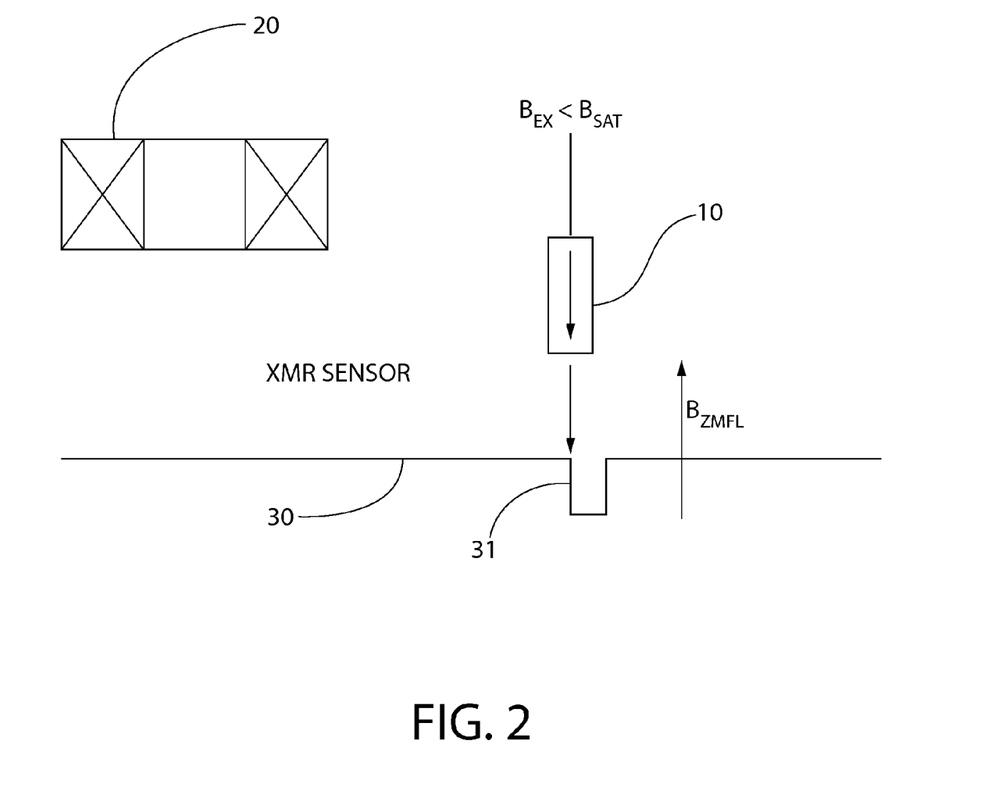
FIG. 2 is a diagram of an area under test with an XMR sensor aligned orthogonal to $B_{ZMFL}$.

This configuration of XMR 10 to the surface of the AUT 30 does not lead to the same signal morphology in response to a material defect 31 as a wound pancake inductive coil ECT probe. Signal morphology is a critical ECT product requirement as there is often continuity required with historic inspection data. A pancake coil based ECT probe does a spatial integration of the time rate of change of all three axes of magnetic flux leakage at any point in space created by perturbation of the eddy current distribution by a discontinuity in the material. Because the largest vector component $B_{ZMFL}$ of the of the out-of-plane MFL will be the component orthogonal to the AUT, it is the most dominant component in the coils' spatial integration and thus influences most the eddy current signal response. This is best approximated by vertical sensing methodologies (in Cartesian coordinates or radial in cylindrical coordinates) that align the easy axis of the XMR sensor with this field component of the MFL as shown in FIG. 2.

Because of the aforementioned reasons, to date, there has not been a practicable ECT probe that orients an XMR sensor with the easy axis aligned orthogonal to the surface of the AUT.

SUMMARY OF THE INVENTION

In an embodiment of the invention there is device for eddy current based nondestructive testing of tubular structures made of electrically conductive materials wherein the device includes: a plurality of excitation electromagnets having an axis of symmetry and magnetoresistive sensors having an easy axis for magnetic field sensing, The magnetoresistive sensors are arranged in a circular array on a single plane with said the axis aligned radially with respect to the circular pattern and the electromagnets are arranged in a circular pattern on both sides of the plane with their axes of symmetry being arranged parallel to the plane and orthogonal to radii of the circular pattern on which the electromagnets are placed. In a further embodiment, the magnetoresistive sensors are either anisotropic magnetoresistive or giant magnetoresistive sensing elements. In a further embodiment, the excitation electromagnets are wound on coils having a substantially rectangular cross section with four faces and wherein the electromagnets are arranged with one of their faces aligned along at the perimeter of the circular pattern. In a further embodiment, the sensors are mounted between a pair of parallel circular printed circuit boards, the electromagnets are mounted on opposite faces of the printed circuit boards from the sensors and electrical connections to the sensors and the electromagnets are made through the printed circuit boards. In a further embodiment, the excitation electromagnets are arranged to be energized individually. In a further embodiment, a subset of the excitation electromagnets are excited together to create a continuous azimuthally orientated eddy current distribution an area under test. In a further embodiment, a subset of the excitation electromagnets are excited together and a second subset are not excited so as to create an axially oriented eddy current distribution to an area under test. In a further embodiment, the electromagnets are arranged in a substantially staggered pattern such that no two electromagnets on either side of said circular plane are directly opposite each other.

In an embodiment of the invention there is a device for eddy current based nondestructive testing of an article made of electrically conductive materials, which includes: a plurality of excitation electromagnets, each having an axis of symmetry and magnetoresistive sensors having an easy axis for magnetic field sensing. The excitation electromagnets are arranged to induce an eddy current in the article and the magnetoresistive sensors are arranged such that the easy axis is substantially orthogonal to the axis of symmetry. In a further embodiment, the excitation electromagnets are wound on coils having a substantially rectangular cross section with four faces and wherein said electromagnets are arranged with one of their faces aligned to be substantially parallel to a surface of the article, while the sensor are arranged with their easy axes substantially orthogonal do the surface. In a further embodiment, the magnetoresistive sensors are either anisotropic magnetoresistive or giant magnetoresistive sensing elements.

In an embodiment of the invention there is a method of non-destructively testing an article made of electrically conductive material. The method includes the steps of: inducing an eddy current in the article, the eddy current having a direction; sensing the eddy current with either anisotropic magnetoresistive or giant magnetoresistive sensing elements, the sensing elements having an easy axis for magnetic field sensing; and aligning the sensing elements with the easy axis substantially orthogonal to the eddy current direction so as to sense any magnetic flux caused by flaws in the article. In a further embodiment, the article is a tube and the direction is either an axial direction or a circumferential direction. In a further embodiment, the sensing elements in a circular pattern in one plane at the perimeter of a cylindrical probe with said easy axis arranged in a radial direction. In a further embodiment, the excitation coils are arranged around the perimeter on either side of the plane of sensing elements.

The invention will be illustrated in more detail with reference to the following embodiments, but it should be understood that the present invention is not deemed to be limited thereto.

The following exemplary eddy current testing (ECT) probe will locate and characterize flaws or material defects in a conductive material. A novel configuration of square or rectangular eddy current excitation coils and anisotropic magnetoresistive (AMR) or giant magnetoresistive (GMR) sensors is used to perform an ECT. AMR sensors and GMR sensors are referred to as "XMR" sensors in this submission.

Figure 3:
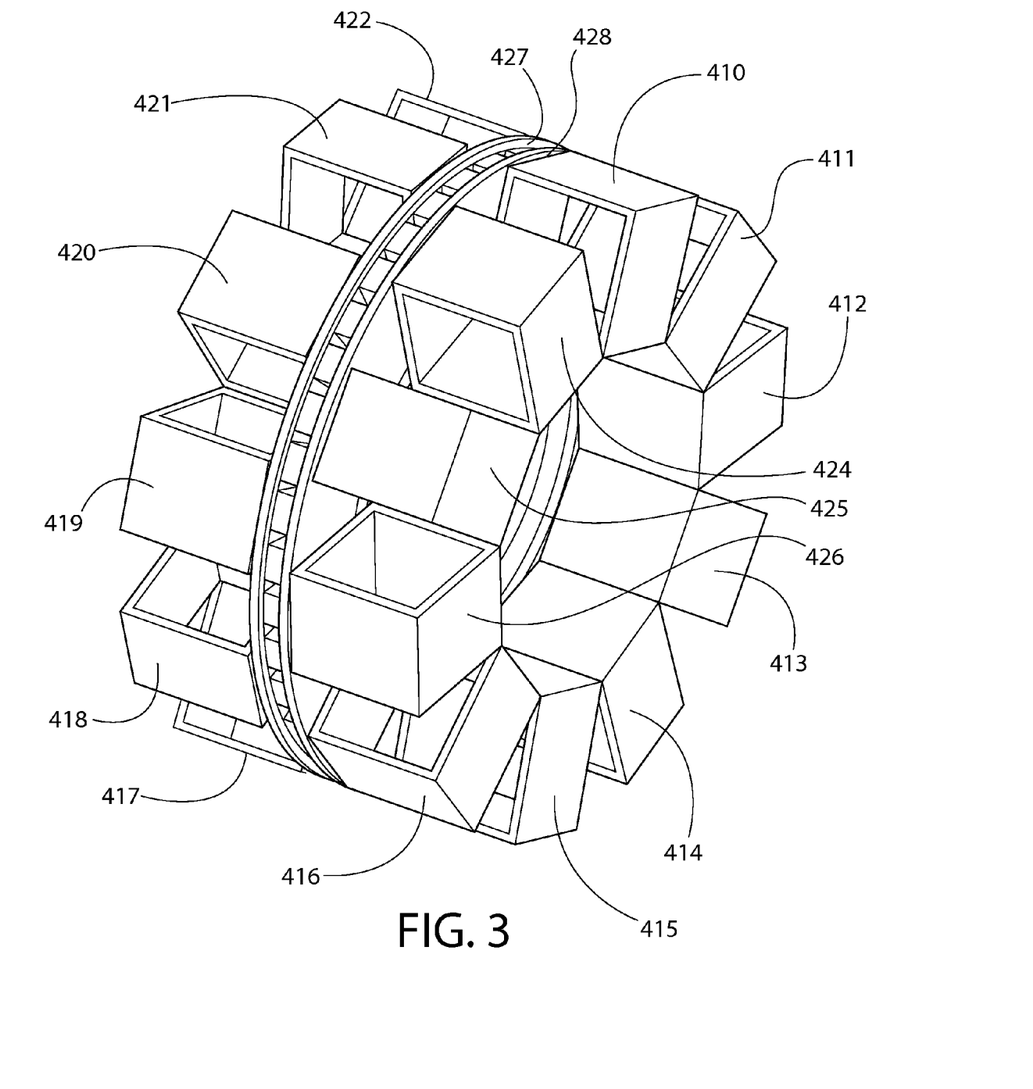
FIG. 3 is a 3D view of an exemplary ECT probe sensor and excitation coil assembly.
Figure 7:
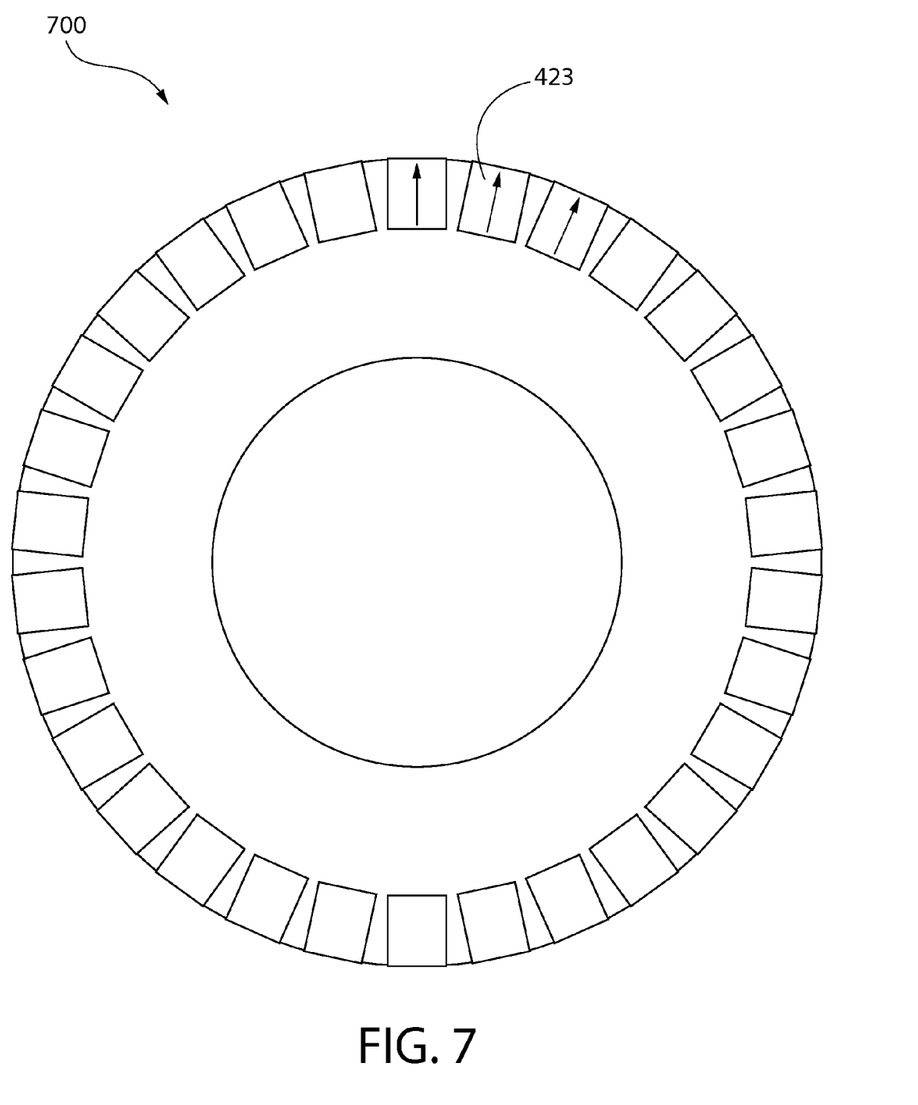
FIG. 7 is a diagram of an exemplary sensor array.

With reference to FIG. 3, in an embodiment, the present invention multiplexes square or rectangular drive coils (410-422) as well as XMR sensors sandwiched between two printed circuit boards 427, 428 to sense of both axial and circumferential flaws within the conductive material volume. This is accomplished by creating an excitation magnetic field distribution used to generate the desired eddy current field in the AUT with regions containing no radial component $B_r$ of the excitation field. With reference to FIG. 7, the XMR elements 423 are positioned in these regions of no $B_r$, with the sensing or "easy" axis radially aligned as shown by the arrows in FIG. 7, thus not interfering with the ability to sense the magnetic field of interest due to sensor saturation.

Due to this novel design attribute, the inventive sensor requires no flux-focusing lens or shielding object to magnetically separate the XMR sensor from the excitation field to prevent saturation by the excitation field. The information acquired via radial sensing will contain traditional in-phase and quadrature (I/Q) information with a signal morphology that is closest to that generated in contemporary wound coil based eddy current testing due to the orientation of the sensor easy axis with the radial component of the AUT MFL.

In an embodiment illustrated in FIGS. 3, 4 and 7, a novel orientation and array distribution of square or rectangular drive coils 410-422 and silicon die level XMR sensing elements 423 are distributed on printed circuit boards 427, 428 as surface mounted devices and subsequently embodied into and ECT probe for tubular material inspection.

This configuration of XMR to the surface of the AUT does not lead to the same signal morphology in response to a material defect as a wound pancake inductive coil ECT probe. Signal morphology is a critical ECT product requirement as there is often continuity required with historic inspection data. A pancake coil based ECT probe does a spatial integration of the time rate of change of all three axes of magnetic flux leakage at any point in space created by perturbation of the eddy current distribution by a discontinuity in the material. Because the largest vector component of the of the out-of-plane MFL will be the component orthogonal to the AUT, it is the most dominant component in the coils' spatial integration and thus influences most the EC signal response. This is best approximated by vertical sensing methodologies (in Cartesian coordinates or radial in cylindrical coordinates) that aligns the easy axis of the XMR sensor with this field component of the MFL.

Figure 4:
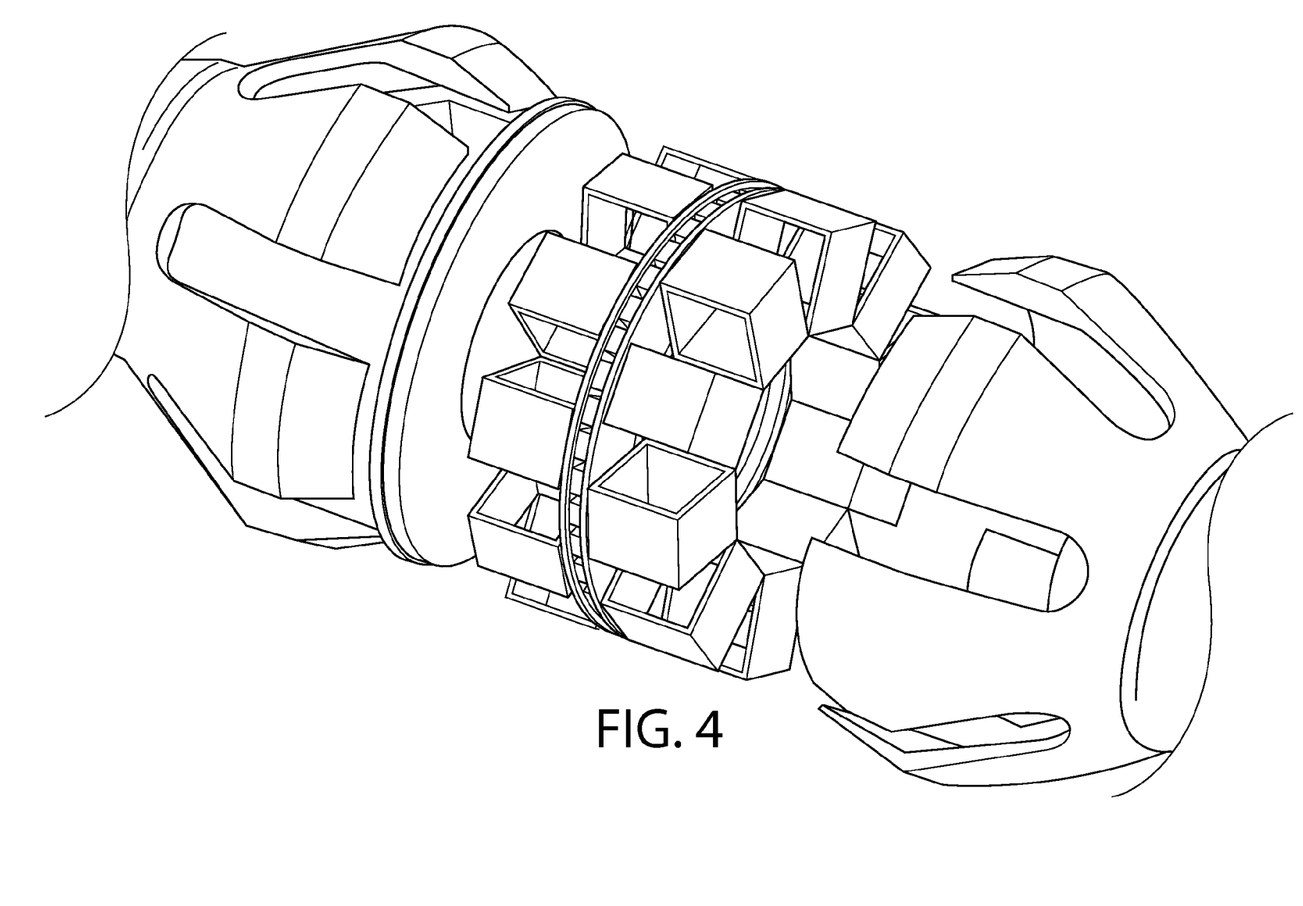
FIG. 4 is a 3D view of an exemplary ECT probe including the assembly of FIG. 3.

As shown in FIGS. 3 and 7, an embodiment of the invention uses an array 700 of XMR sensing elements 423 and inductive wound excitation coils 410, 411 etc. distributed onto a printed circuit board 427, 428 and embodied in a cylindrical probe housing FIG. 4. to sense magnetic flux leakage caused by a discontinuity or flaw in the material in a given AUT. The individual XMR sensors 423 will have their easy axis oriented radially with respect to the cylindrical orientation of the AUT with respect to the probe as shown by the arrows in FIG. 7. This invention will create a distribution of excitation coils and sensing elements that will have minimized interaction between the sensor and the excitation field without necessitating magnetic shielding or flux concentrators in the AUT.

Figure 5:
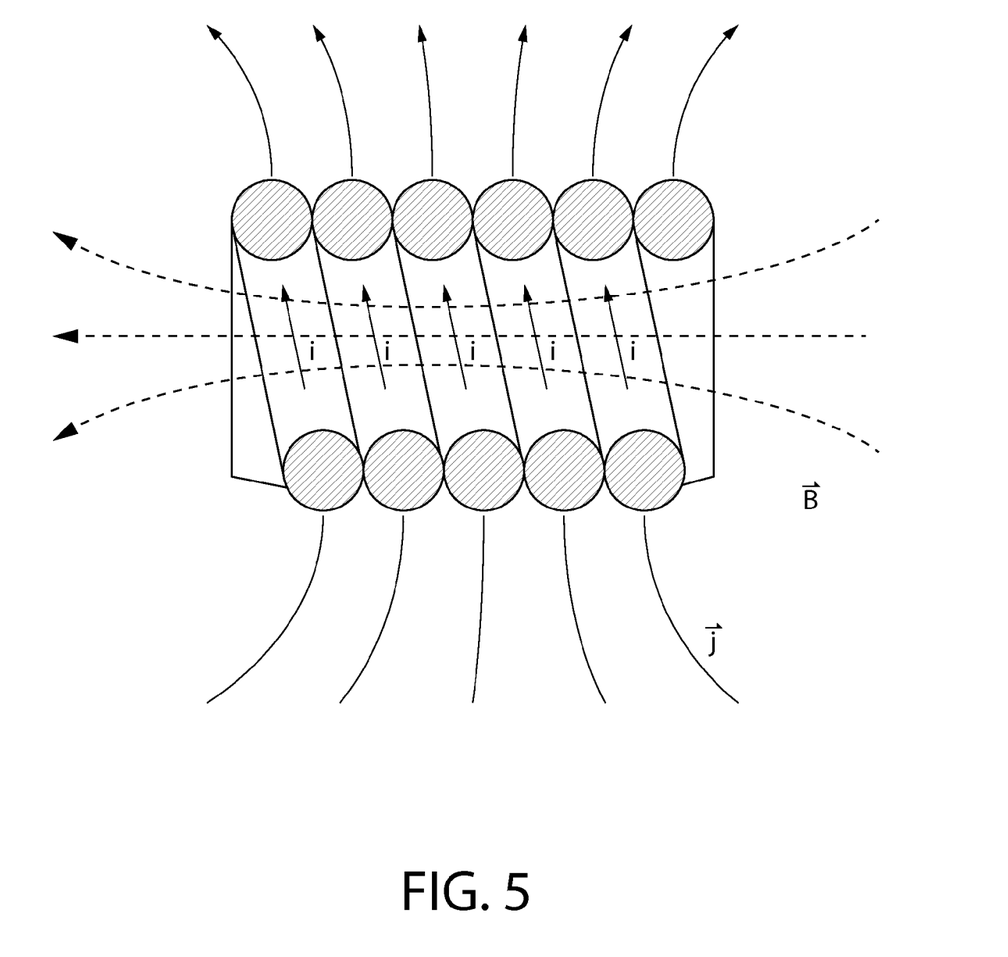
FIG. 5 is a diagram of a prior art excitation coil.
Figure 6:
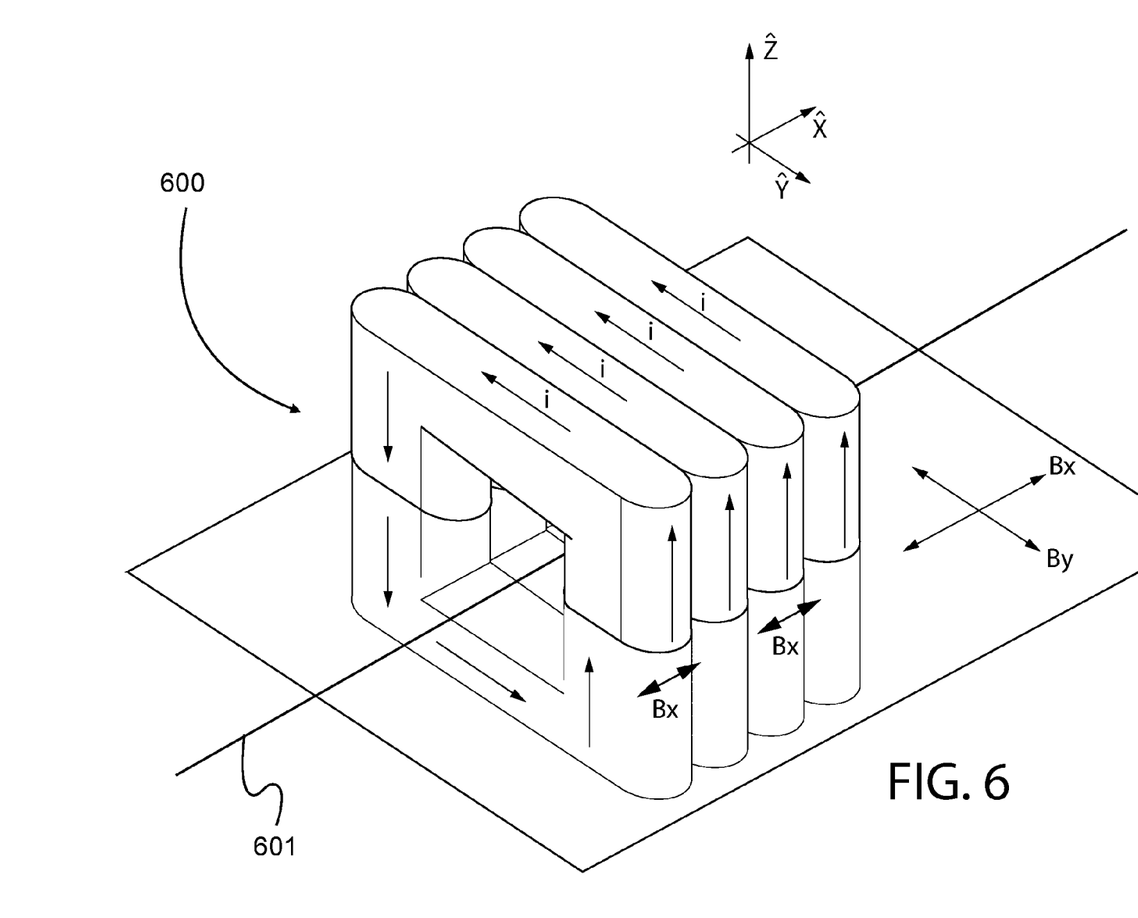
FIG. 6 is a diagram of an exemplary coil having a square bobbin shape.

In an embodiment shown in FIG. 6, the excitation coils are square or rectangular to create magnetic fields $B_X$, $B_Y$ with controlled vector orientations to optimize sensor sensitivity via minimization of the impinging background excitation field. This is in contrast to a prior art circularly wound coil as shown in FIG. 5. Prior art methodology as shown in FIG. 1 is to place the XMR sensor 10 in the center of the drive coil 20 with the sensitive axis shown by the arrow orthogonal to the excitation field. This limits the sensor to horizontal sensing and limits spatial resolution as well, since the excitation coil geometry becomes the array resolution constraint. By optimization of the excitation field and creating controlled regions of no excitation field, the excitation coil and the sensor can be physically separated thus creating a spatial resolution only constrained by the sensor die size.

Figure 8:
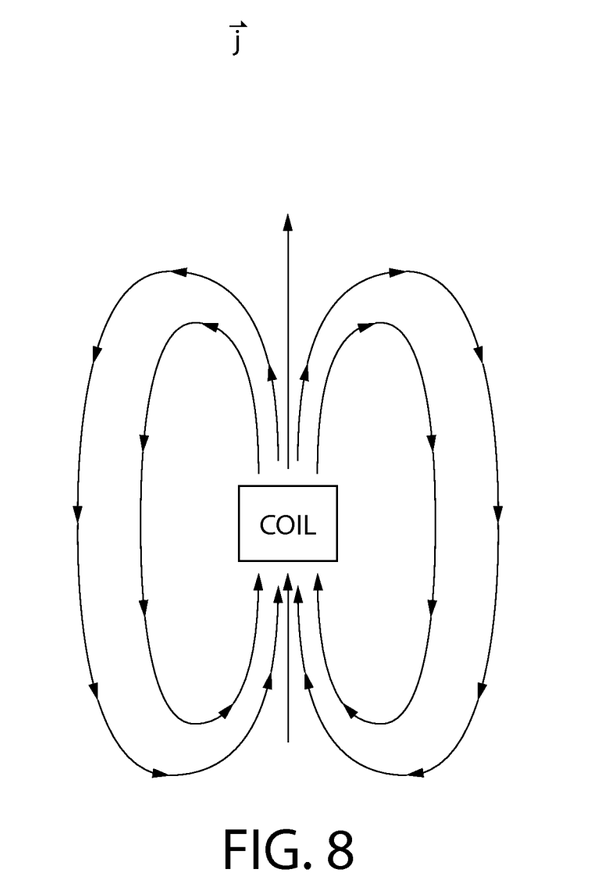
FIG. 8 is a diagram of an exemplary eddy current vector in an area under test.
Figure 9:
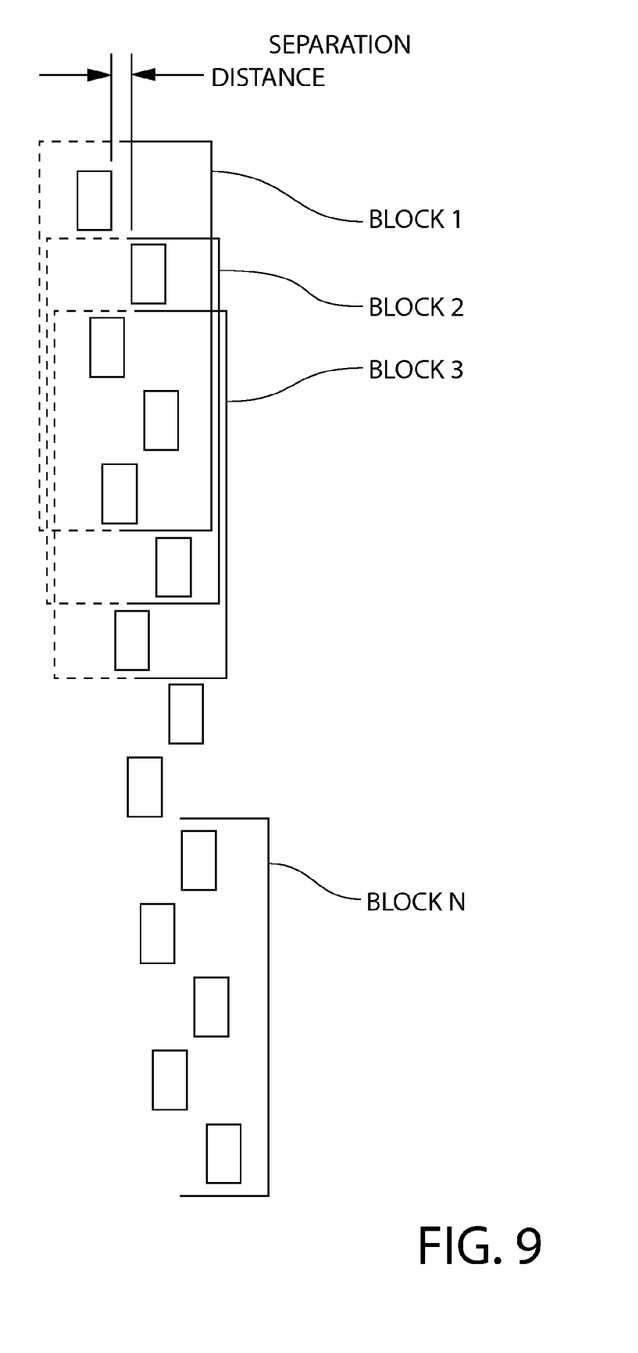
FIG. 9 is diagram of sequenced blocks of eddy current excitation coils as viewed around the perimeter of an exemplary probe such as is shown in FIG. 3.
Figure 10:
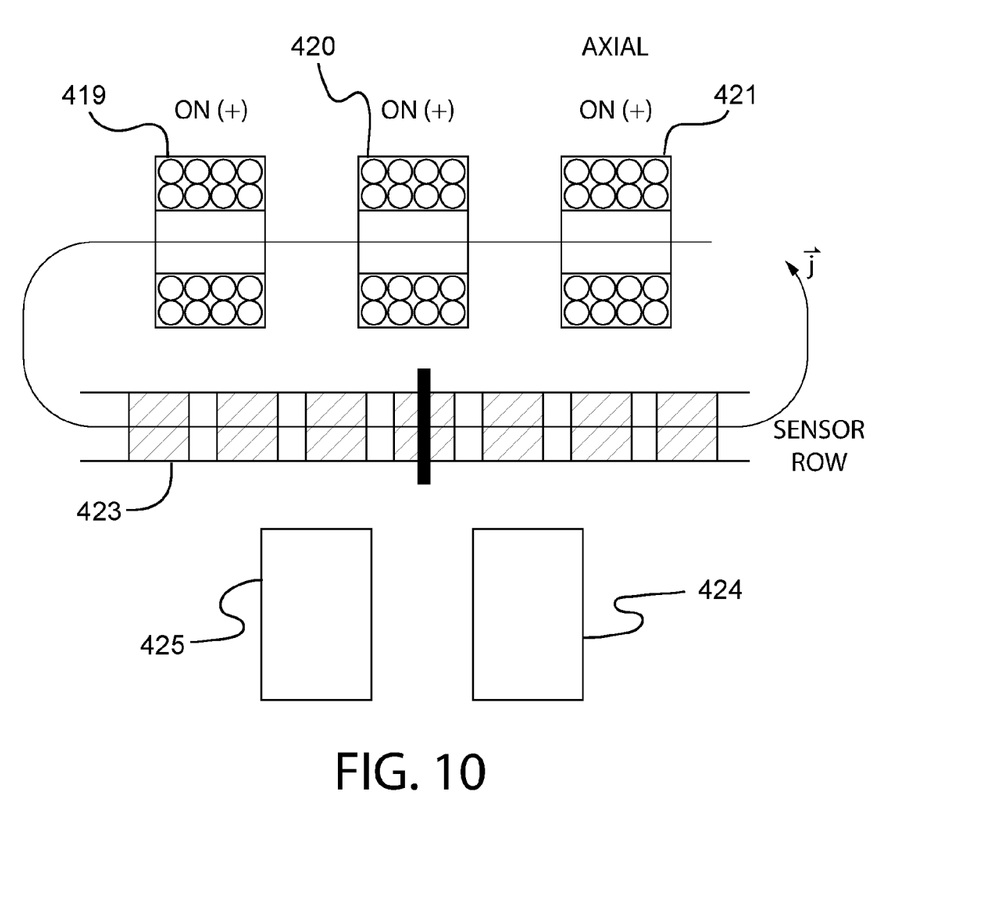
FIG. 10 is a diagram of an excitation mode for an exemplary block of coils to create a circumferential eddy current flow to sense an axial flaw.

In an embodiment, a plurality of multi-turn square or rectangular excitation coils, an example 600 of which is shown in FIG. 6, are oriented orthogonally to the surface (the axis of coil symmetry 601 orthogonal to the surface normal) of inspection oriented in a manner that will individually generate a dipole magnetic field and a subsequent eddy current distribution underneath (this pattern is very similar to that generated by a D-coil pencil probe or D-shaped planar coil). A typical response in a material under test is shown in FIG. 8. An array of square or rectangular drive coils oriented with respect to a distribution of XMR sensing elements illustrated in FIGS. 3 and 7 can be configured to stimulate both axial as well as circumferential flaw sensing eddy current vectors in the AUT when sequentially fired via multiplexing circuitry. Coils energized as shown in FIG. 10 will create the necessary eddy current distribution for axial flaw (direction of black bar in FIG. 10) sensing by simultaneous actuation of sets of coils around the circumference. For "circumferential" (azimuthal angle $\phi$) eddy current generation in the AUT, current is supplied to excitation coils on one side of the sensor row simultaneously and equally activated. This simultaneous activation of coils will create a continuous azimuthally orientated eddy current distribution the area under test.

Figure 11:
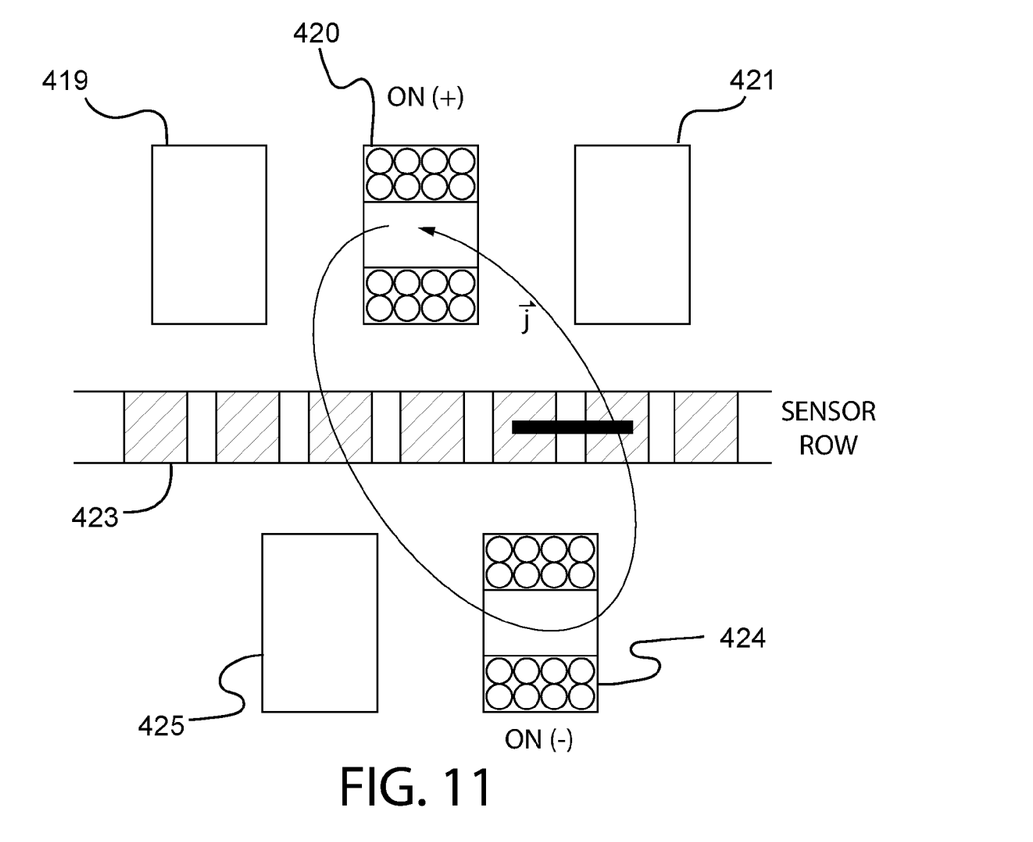
FIG. 11 is a diagram of an excitation mode for an exemplary block of coils to create an axial eddy current flow to sense a circumferential flaw.

Coils energized as shown in FIG. 11, i.e. on opposite sides of the sensor row, create the necessary axial orientation of eddy currents for sensing circumferential flaws in a cylindrical area under test. Note that in this mode, the coils are energized to create opposing directions of current j.

In a further embodiment, off-the-surface sensing via XMR can be performed by incorporation of drive coils that have enough amp-turns to create an adequate signal-to-noise ratio in the sensed MFL.

This distribution of same directional current carrying wires in excitation coils creates a region that has a longitudinal magnetic field and zero transverse magnetic field (along the direction of the current carrying wire) external to the solenoid face. This region will have no Br in cylindrical coordinates. There are two novel attributes to this coil arrangement: (a) it allows both axial as well as circumferential eddy current distribution; and (b) the array configuration allows for regions of zero (or significantly reduced) excitation Br, thereby allowing the efficient use and placement of the XMR elements for vertical (radial) sensing of magnetic flux leakage field due to the flaw of interest.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and various embodiments with various modifications as are suited to the particular use contemplated.

Utilization of XMR sense elements as described herein will have the following useful aspects. It will increase spatial resolution in the pick-up array via individual sensing elements that are on the order of 0.5 mm to 1 mm in width at the silicon die level. It will also increase inspection sensitivity as these sensors have an increased sensitivity over wound pancake coil receive sensors. It will also increase image quality in a multi-frequency scan due to XMR sensor sensitivity not being a function of the frequency of magnetic field sensed (versus prior art inductive sensing elements). It will provide the ability of vertical (radial for tubular applications) XMR sensing allowing the use of an XMR sensing element to best approximate the signal morphology created by a wound pancake coil receiver. It will enable axial as well as circumferential flaw sensing and characterization. It will enable off-the-surface (non-contact) sensing. In addition, no shielding of the XMR sensor from the excitation signal is necessary.

Utilization of the novel drive coil configuration in this submission will: Generate eddy currents with a net directional vector that is in the Z direction (in cylindrical coordinates) for circumferential indication detection; generate eddy currents with a net directional vector that is on the azimuthally oriented (in cylindrical coordinates) for axial indication detection; and allow the use of XMR sensors in close proximity of the drive coil without saturation.

Operation of the Present Invention may be as Follows:

Uni-directional XMR sensors 423 are placed between the excitation coils in a manner outlined above and shown in FIGS. 3.and 7. The sensing elements 423 will be oriented between the excitation coils 410-422 with the sensor easy axis, shown by arrows in FIG.7, oriented orthogonally to the area under test. For a cylindrical application (tube inspection) this orientation would be in the radial direction as shown in exemplary sensor array 700 in FIG. 7. Excitation coils and 410-422 and sensors in the proximity of the area of interest can be activated to execute material inspection in this region. The array of sensors and excitation coils can be processed in groups to cover the entire area under test for either axial or circumferential flaw detection. For example, with reference to FIG. 3, coils 421 and 424 can be activated as shown in FIG. 11 and resulting eddy currents sensed. Then coils 420 and 413 can be activated. Next coils 419 and 426, and so on to cover the entire circumference of the sensor. Similarly staged sets of coils as shown in FIG. 10 on one side of the sensor row (e.g. 421, 420, 419 then 420, 419, 418 etc.) can be sequentially energized for sensing axial flaws.

For circumferential eddy current generation in the AUT to sense axial flaws as shown in FIG. 10, current is supplied to banks of excitation coils on one side of the sensor row. These banks of coils will be simultaneously and equally activated. These banks will then be multiplexed and sequentially driven to encompass the area under test as shown in FIG. 10.

For sensing a circumferential (azimuthal angle $\phi$) flaw in the AUT, current is supplied to excitation coils on opposite sides of the sensors. The coils are simultaneously activated to create opposite field directions as shown in FIG. 11, wherein the black horizontal bar indicates the orientation of a flaw. This simultaneous activation of coils across the sensor row will create a continuous azimuthally orientated eddy current distribution the area under test.

These eddy currents when perturbed by a material discontinuity (flaw, crack, variation in crystal structure, variation in material phase resulting in a permeability variation) will create a variation in the reciprocal magnetic field. This magnetic field directly associated with the eddy current is sensed via the XMR sensor to create a direct mapping of the magnetic field variation in an area of interest. From these variations intelligence regarding flaw, crack, and variation in crystal structure, variation in material phase resulting in permeability variations can be inferred.

This embodiment will use vertical (or radial in cylindrical coordinates) sensing to best approximate the signal response of an inductive wound coil magnetic sensor currently and most commonly used in eddy current testing (ECT).

While the invention has been described in detail and with reference to specific examples thereof, it will be apparent to one skilled in the art that various changes and modifications can be made therein without departing from the spirit and scope thereof.

What is claimed is:

1. A device for eddy current based nondestructive testing of a tubular structure made of electrically conductive materials comprising:
    a plurality of excitation electromagnets each having an axis of symmetry about which a coil of electrically conductive material is formed; and
    magnetoresistive sensors having an easy axis for magnetic field sensing;
    wherein said magnetoresistive sensors are arranged in a circular pattern on a single plane;
    wherein said easy axis for each of said magnetoresistive sensors is aligned radially with respect to said circular pattern and configured to sense, by change in electrical resistance, a magnetic field excited by said electromagnets and altered by the tubular structure under test; and
    wherein said excitation electromagnets are arranged in a circular pattern on both sides of said plane with their axes of symmetry being arranged parallel to said plane and orthogonal to radii of said circular pattern on which said electromagnets are placed.

2. The device of claim 1, wherein said magnetoresistive sensors are either anisotropic magnetoresistive or giant magnetoresistive sensing elements.

3. The device of claim 1, wherein said excitation electromagnets are wound on coils having a substantially rectangular cross section with four faces and wherein said electromagnets are arranged with one of their faces aligned along at the perimeter of said circular pattern.

4. The device of claim 1, wherein said sensors are mounted between a pair of parallel circular printed circuit boards, said electromagnets are mounted on opposite faces of said printed circuit boards from said sensors and wherein electrical connections to said sensors and said electromagnets are made through said printed circuit boards.

5. The device of claim 1, wherein said excitation electromagnets are arranged to be energized individually.

6. The device of claim 1, wherein a subset of said excitation electromagnets are excited together to create a continuous azimuthally orientated eddy current distribution in an area under test.

7. The device of claim 1, wherein a subset of said excitation electromagnets are excited together to create an axially oriented eddy current distribution in an area under test.

8. The device of claim 1, wherein said excitation electromagnets are arranged in a substantially staggered pattern such that no two electromagnets on either side of said circular plane are directly opposite each other.

9. A device for eddy current based nondestructive testing of an article having a surface to be tested and made of electrically conductive materials comprising:
    a plurality of excitation electromagnets each having an axis of symmetry about which a coil of electrically conductive material is formed, and
    magnetoresistive sensors having an easy axis for magnetic field sensing;
    wherein said excitation electromagnets are arranged with said axes of symmetry oriented orthogonally to the surface of the article to induce an eddy current in the article and wherein said magnetoresistive sensors are arranged such that said easy axis for each magnetoresistive sensor is substantially orthogonal to said axes of symmetry and configured to sense, by change in electrical resistance, a magnetic field excited by said electromagnets and altered by the article under test.

10. The device of claim 9, wherein said excitation electromagnets are wound on coils having a substantially rectangular cross section with four faces and wherein said electromagnets are arranged with one of their faces aligned to be substantially parallel to a surface of the article.

11. The device of claim 9, wherein said magnetoresistive sensors are either anisotropic magnetoresistive or giant magnetoresistive sensing elements.

12. A method of non-destructively testing an area of an article made of electrically conductive material comprising:
    inducing, with a plurality of electromagnets, an eddy current in said article, said eddy current having a direction;
    sensing said eddy current with either anisotropic magnetoresistive or giant magnetoresistive sensing elements, said magnetoresistive sensing elements having an easy axis for magnetic field sensing and producing a change in electrical resistance in response to said magnetic field; and
    aligning said magnetoresistive sensing elements with said easy axis substantially orthogonal to said eddy current direction and to the area under test, so as to sense any magnetic flux caused by flaws in the article.

13. The method of claim 12 wherein said article is a tube and said direction is either an axial direction or a circumferential direction.

14. The method of claim 13, further comprising arranging said sensing elements in a circular pattern in one plane at the perimeter of a cylindrical probe with said easy axis arranged in a radial direction.

15. The method of claim 14, further comprising arranging excitation coils around said perimeter on either side of said plane of sensing elements.

\* \* \* \* \*